US008389273B2

(12) United States Patent
Yu et al.

(10) Patent No.: US 8,389,273 B2
(45) Date of Patent: Mar. 5, 2013

(54) POLYMERASE CHAIN REACTION METHOD, POLYMERASE CHAIN REACTION DROPLET DEVICE, AND POLYMERASE CHAIN REACTION DROPLET DEVICE ARRAY

(75) Inventors: Chih-Sheng Yu, Hsinchu (TW); Yi-Chiuem Hu, Hsinchu (TW); Fan-Gang Tseng, Hsinchu (TW)

(73) Assignee: National Applied Research Laboratories, Taipei (TW)

( * ) Notice: Subject to any disclaimer, the term of this patent is extended or adjusted under 35 U.S.C. 154(b) by 154 days.

(21) Appl. No.: 12/703,209

(22) Filed: Feb. 10, 2010

(65) Prior Publication Data

US 2011/0159547 A1 Jun. 30, 2011

(30) Foreign Application Priority Data

Dec. 29, 2009 (TW) ............................... 98145667 A

(51) Int. Cl.
*C12M 1/34* (2006.01)
*C12M 3/00* (2006.01)
*C40B 60/08* (2006.01)
*C12Q 1/68* (2006.01)

(52) U.S. Cl. ........................ 435/287.2; 506/37; 435/6.12

(58) Field of Classification Search ........................ None
See application file for complete search history.

(56) References Cited

U.S. PATENT DOCUMENTS 5,819,842 A * 10/1998 Potter et al. .................... 165/206
6,572,830 B1 * 6/2003 Burdon et al. ........... 422/186.29
6,737,024 B1 * 5/2004 Eipel et al. .................... 502/407
2002/0110492 A1 * 8/2002 Handique ...................... 422/100
2002/0163414 A1 * 11/2002 Mayer et al. ................... 336/199
2003/0091809 A1 * 5/2003 Scarborough et al. ..... 428/304.4
2006/0191887 A1 * 8/2006 Baer et al. ...................... 219/219
2008/0274511 A1 * 11/2008 Tan et al. ...................... 435/91.2
2009/0264317 A1 * 10/2009 Ofir et al. ........................ 506/16

OTHER PUBLICATIONS

Yoon et al. (2002) J. Micromech. Microeng. 12: pp. 813-823 ).*
Bu et al. (2003) J Micromech Microeng. 13: S125-S130.*
Lou et al. (2004) BioTechniques 36:248-252.*
Wetmur et al. (2005) Nucleic acid res vol. 33 No. 8 pp. 2615-2619.*
Diehl et al. (2006) Nature methods vol. 3 No. 7 pp. 551-559.*
Lee et al. (2000) Anal. Chem. vol. 72: 4242-4247.*
TIBTEC Innovations [online] [retrieved on Jul. 2012] retrieved from http://www.tibtech.com/conductivity.php.*

* cited by examiner

*Primary Examiner* — Samuel Woolwine
*Assistant Examiner* — Suchira Pande
(74) *Attorney, Agent, or Firm* — WPAT, P.C.; Anthony King

(57) ABSTRACT

The present invention discloses a polymerase chain reaction (PCR) method, a PCR droplet device and a PCR droplet device array. The steps of the method comprise that a liquid comprising an analyzer is dropped on the heating coil disposed on the droplet device to form a droplet, then dropping a hydrophobic solution to prevent the droplet from evaporating. When an electric current or a voltage is supplied through at least one conducting wire to heat the heating coil, the inside of the droplet can generate buoyancy to drive the analyzer to move to the top of the inside of the droplet. Subsequently, the analyzer is moved to a periphery of the inside of the droplet so as to form a thermal cycle. Therefore the template is amplified by recycling the thermal cycle.

17 Claims, 5 Drawing Sheets

POLYMERASE CHAIN REACTION METHOD, POLYMERASE CHAIN REACTION DROPLET DEVICE, AND POLYMERASE CHAIN REACTION DROPLET DEVICE ARRAY

FIELD OF THE INVENTION

The present invention relates to a polymerase chain reaction (PCR); and more particularly, to a PCR method, a PCR droplet device and a PCR droplet device array.

BACKGROUND OF THE INVENTION

The polymerase chain reaction (PCR) was invented by Kary Mullis in 7985, and Mullis thus was awarded the Nobel Prize and obtained patent rights about the PCR (U.S. Pat. No. 4,683,195 and U.S. Pat. No. 4,683,202). The PCR is patentable because the PCR is an invention not a discovery, in other words, the biochemical reaction thereof is not existed in the nature. The PCR is a man-made reaction, and is applied to pair a DNA double helix and bases. There are two functions, four kinds of materials, and three step circulation in the PCR procedure. The two functions of the PCR are searching and replication. Via the PCR procedure, a specific base sequence having hundreds of base pairs (bps) can be searched out from nucleic acid molecules having millions upon millions of base pairs, and the specific base sequence can be replicated into more than one million duplications. The four kinds of materials are a DNA template, a pair of primers, deoxyribonucleotide triphosphates (dNTPs) and a polymerase. The primers are also called as nucleic molecules, and the length of the primer is in a range of about 25 to 30 bps.

Furthermore, the PCR procedure comprises the three steps as follows. (1) Denaturation step: the double strand DNA melts to single strand DNA at the temperature of 95° C. (2) Annealing step: the reaction temperature is decreased to about 30 to 65° C. to allow the primers to anneal with the complementary single strand DNA. (3) Extension step: the temperature is increased to about 65 to 75° C. to activate the DNA polymerase. At this step, the DNA polymerase synthesizes a new DNA strand complementary to the original DNA strand via adding dNTPs which are complementary to the original DNA strand in 5' to 3' direction. The three steps as set forth are called a cycle. The PCR procedure is accomplished to amplify a specific region of a DNA strand by adjusting cycles.

The PCR technique can be classified into a continuous movement of liquid and a stationary liquid. In a prior art of the continuous movement of liquid, the PCR device is manufactured by using three metal pieces to form three different temperature areas. The feature thereof is that a specific flow channel is formed on a glass substrate to provide a liquid to flow, and three different heat sources are disposed under the glass substrate to form the three different temperature areas. Therefore, when the liquid is dropped on the specific flow channel, the liquid can be flowed through the three different temperature areas by an external pump so as to accomplish the PCR procedure. Because the liquid is driven by the external pump, the external pump may increase the difficulty in the minimization manufacture.

Additionally, in a prior art of the stationary liquid (Science, vol 298, page 739, 2002), the PCR device comprises the water cooled top plate, the hot plate, and the two cubes. The water cooled top plate and the hot plate are respectively disposed on the top of the two cubes and the bottom of the two cubes. The sealed cavity is formed in the intermediate space of the two cubes to contain a liquid comprising an analyzer. The two different temperature plates, the water cooled top plate and the hot plate, can generate the temperature differences to drive the liquid to flow, and thus, to amplify the analyzer, such as a specific template. Furthermore, in another prior art, the PCR process is performed by an optical heating method (Physical Biology, vol 1, page 1-8, 2004). The optical heating method is achieved by using a far infrared ray to focus on a liquid, such that the temperature of the liquid can be increased to accomplish the PCR procedure. The optical heating method requires an optical system and an alignment device; it will increase difficulties on integrating with the optical system and the alignment device.

SUMMARY OF THE INVENTION

In view of the aforementioned drawbacks in prior art, an object of the present invention is to provide a polymerase chain reaction (PCR) method, a PCR droplet device and a PCR droplet device array, so as to accomplish the template amplification in short time via controlling a single temperature.

To achieve the above object, the PCR method according to the present invention comprises the following steps. A liquid comprising an analyzer is dropped onto a heating coil disposed on a droplet device so as to form a droplet. The analyzer comprises a template, a primer, a deoxyribonucleotide triphosphate (dNTP), and a polymerase. Further, a hydrophobic solution is dropped onto a surface of the droplet to prevent the liquid from evaporating. Finally, an electric current or a voltage is applied through at least one conducting wire disposed on the droplet device to heat the heating coil. Therefore, buoyancy in an inside of the droplet is generated, thereby driving the analyzer to move to a top of the inside of the droplet, and subsequently to move to a periphery of the inside of the droplet so as to form a thermal cycle.

Wherein, a temperature of a center of a bottom of the droplet is in a range of 90° C. to 100° C. to denature the template, and the analyzer is moved to the top of the inside of the droplet by the buoyancy. A temperature of the top of the inside of the droplet is in a range of 30 to 65° C. to anneal the primer on a specific position of the template. Subsequently, the analyzer is moved to a side of the bottom of the droplet due to the circular shape of the droplet. A temperature of the side of the bottom of the droplet is in a rage of 65 to 80° C. so as to extend the specific position of the template. Finally, the analyzer is moved back to the center of the bottom of the droplet to form the thermal cycle, such that the template is amplified by recycling the thermal cycle.

Additionally, the PCR droplet device comprises a cooling plate, a substrate, a first containing area, a second containing area, a heating coil, at least one conducting wire, and a plurality of sensors. The substrate is disposed on the cooling plate. The heating coil, the at least one conducting wire, the plurality of sensors, the first containing area, and the second containing area are all disposed on the substrate. Further, the heating coil is disposed on the center of the first containing area, and the at least one conducting wire can be connected with the heating coil to detect temperature changes of the heating coil. The first containing area may contain a liquid comprising an analyzer. The second containing area surrounds the first containing area to contain a hydrophobic solution, and the hydrophobic solution can be dropped onto the surface of the liquid to prevent from evaporating.

Wherein, the analyzer comprises a template, a primer, a deoxyribonucleotide triphosphate (dNTP) and a polymerase. When the at least one conducting wire is applied with an electric current or a voltage to heat the heating coil, buoyancy in an inside of the liquid is generated. The analyzer is driven to move to a top of the inside of the liquid by the buoyancy. Subsequently, the analyzer is driven to move to a periphery of the inside of the liquid so as to form a thermal cycle. Therefore, the template is amplified by recycling the thermal cycle.

Furthermore, a polymerase chain reaction (PCR) droplet device array comprises the plurality of the PCR droplet device as set forth, and the plurality of the PCR droplet device disposed in an array mode.

Accordingly, the polymerase chain reaction (PCR) method, the PCR droplet device and the PCR droplet device array according to the present invention provide one or more of the following advantages:

(1) Because the minimization feature in the PCR method according to the present invention is achieved, the experimental time of PCR procedure can be decrease by using micro-volume solutions comprising analyzers.

(2) In the PCR droplet device according to the present invention, a template amplification reaction is accomplished by controlling a single temperature, which means that the temperature of the heating coil is stationary.

(3) Many kinds of samples can be experimented on the PCR droplet device array according to the present invention. In the meanwhile, the annealing temperatures of kinds of primers can be detected. Thus, it can save the experimental time.

BRIEF DESCRIPTION OF THE DRAWINGS

The structure and the technical means adopted by the present invention to achieve the above object can be best understood by referring to the following detailed description of the preferred embodiments and the accompanying drawings, wherein.

DETAILED DESCRIPTION OF THE PREFERRED EMBODIMENTS

The present invention will now be described with some preferred embodiments thereof with reference to the accompanying drawings. It is understood the experimental data shown in the embodiments are provided only for easy interpretation of the technical means of the present invention and should in no means be considered as restriction to the present invention.

Figure 1:
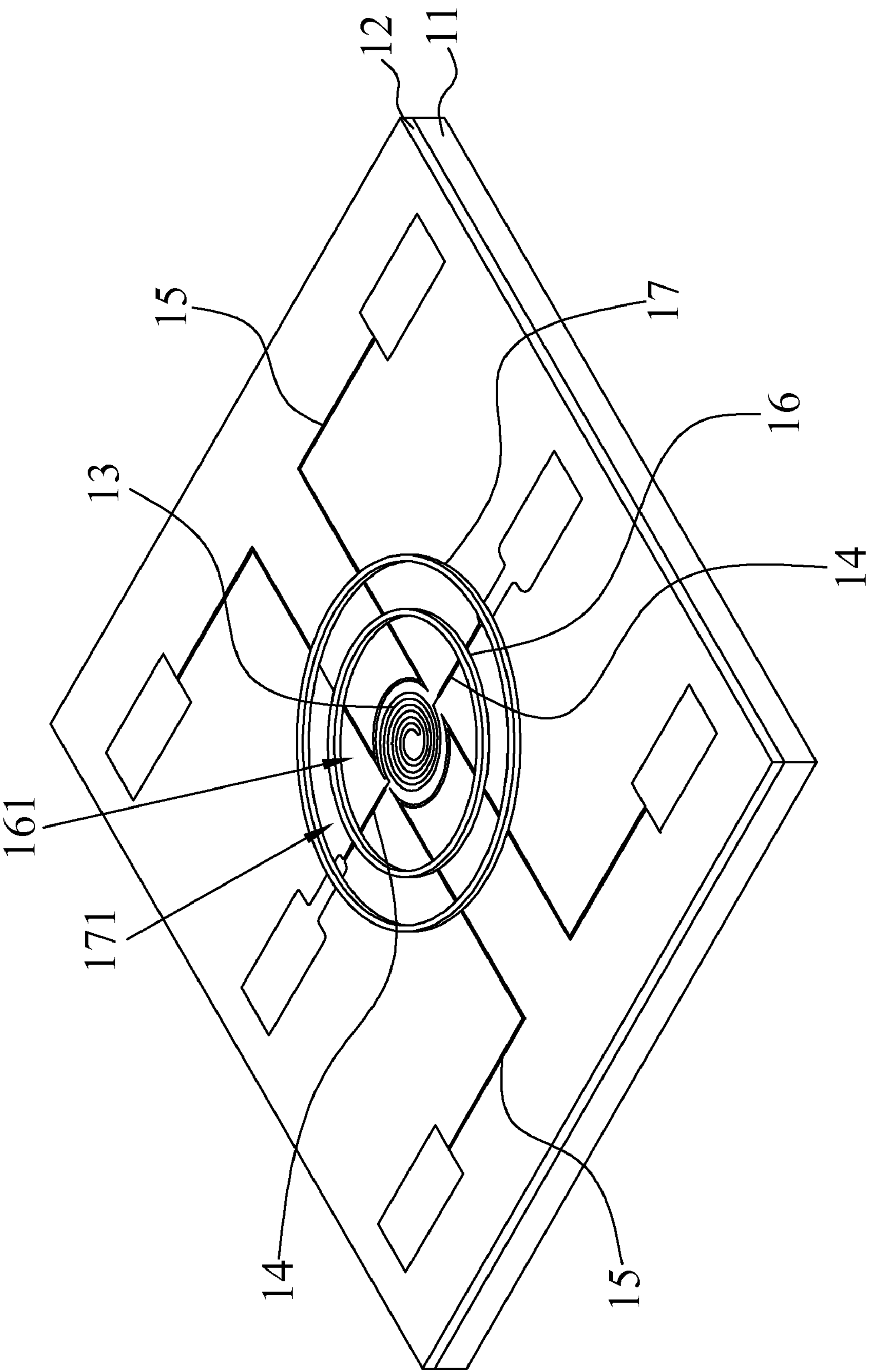
FIG. 1 is a schematic diagram illustrating a polymerase chain reaction (PCR) droplet device according to an embodiment of the present invention.

Please refer to FIG. 1 that is a schematic diagram illustrating a polymerase chain reaction (PCR) droplet device according to an embodiment of the present invention. As shown, the PCR droplet device comprises a cooling plate 11, a substrate 12, a heating coil 13, at least one conducting wire 14, a plurality of sensors 15, a first partition 16, and a second partition 17. The substrate 12 can be disposed on the cooling plate 11. The heating coil 13, the at least one conducting wire 14, the plurality of the sensors 15, the first partition 16, and the second partition 17 are all disposed on the substrate 12. The at least one conducting wire 14 can be connected with the heating coil 13, and the plurality of sensors 15 can be disposed around the heating coil 13 to detect temperature changes of the heating coil 13. Further, the first partition 16 surrounds a periphery of the heating coil 13 to form a first containing area 161, such that a liquid comprising an analyzer can be dropped on the first containing area 161. The second partition 17 surrounds a periphery of the first partition 16 to form a second containing area 171, and a hydrophobic solution is dropped on the second containing area 171.

Figure 2:
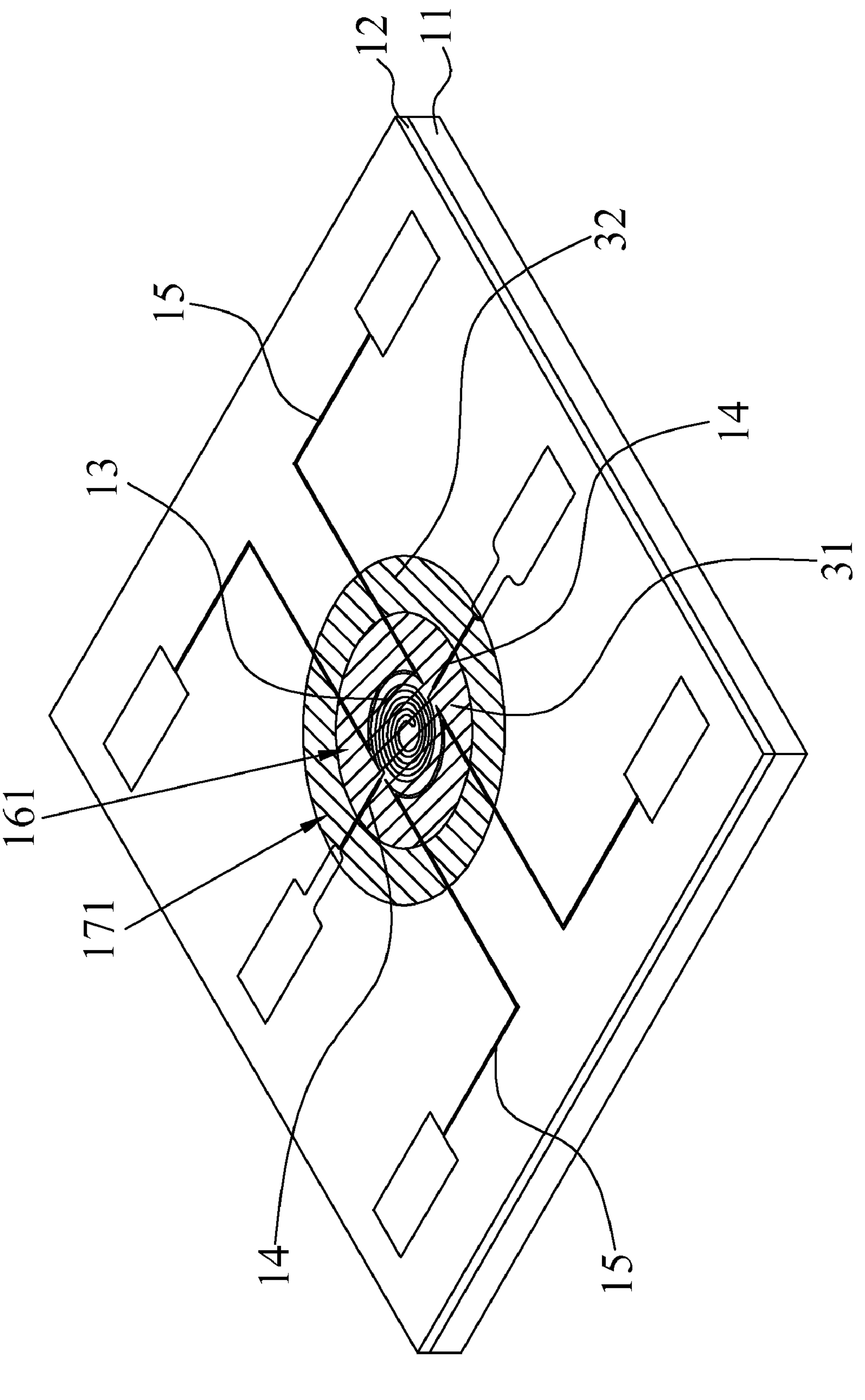
FIG. 2 is a schematic diagram illustrating a PCR droplet device according to another embodiment of the present invention.

Please refer to FIG. 2 that is a schematic diagram illustrating a PCR droplet device according to another embodiment of the present invention. As shown, the surface of the first containing area 161 can be coated with a hydrophilic material 31, and the surface of the second containing area 171 can be coated with a hydrophobic material 32. Because the liquid comprising the analyzer is hydrophilic, the liquid can be immobilized on the hydrophilic material 31 of the first containing area 161 when the liquid is dropped on the first containing area 161. Moreover, the hydrophobic solution and the materials coated on the second containing area 171 is both hydrophilic. When the hydrophobic solution is dropped on the second containing area 171, the hydrophobic solution can be immobilized on the hydrophobic material 32 of the second containing area 171. Thus, without necessary to dispose the first partition 16 and the second partition 17, the liquid can be formed a droplet while dropping the liquid on the first containing area 161. A functional group of the hydrophilic material 31 may comprise a hydrogen group, a carbonyl group, a carboxyl group, hydroxyl group, a sulfonic acid group, or an amino group. The hydrophobic material 32 may comprise epoxide, cyclic acetal, or styrene.

Wherein, said analyzer comprises a template, a primer, a deoxyribonucleotide triphosphate (dNTP) and a polymerase. Glycerol can be further added into the liquid to increase the viscosity of the liquid, and therefore, users can adjust the retention time of the analyzer at the specific temperature. Furthermore, controlling the retention time of the analyzer at the specific temperature can also be performed by adjusting the size of the droplet, i.e. adjusting the size of the first containing area 161 and the size of the second containing area 171. For example, it can be achieved to adjust a distance between the first partition 16 and the heating coil 13, and a distance between the second partition 17 and the heating coil 13, or a width of the hydrophilic material 31 and hydrophobic material 32 respectively coated on the first containing area 161 and the second containing area 171. For instance, the distance between the first partition and the center of the heating coil may be in a range of 0.5 to 2.5 mm, and the distance between the second partition and the center of the heating coil may be in a range of 1 to 3 mm. When the at least one conducting wire 14 is applied with an electric current or a voltage to heat the heating coil 13, the temperature of the bottom 211 of the liquid is increased to result in decreasing the density of the bottom 211 of the liquid, and subsequently, water molecules and the analyzer are moved to the top 212 of the liquid, such that buoyancy in an inside of the liquid is generated. Then, the analyzer is driven to move to a periphery of the inside of the liquid so as to form a thermal cycle. The template is amplified by recycling the thermal cycle.

Preferably, the hydrophobic solution can be mineral oil. The mineral oil usually is used as a solution to prevent the liquid comprising the analyzer from evaporating in the PCR procedure. Thus, the PCR droplet device of the present invention has two designed areas respectively defined by the first partition 16 and the second partition 17 on the substrate 12 in order to contain two kinds of liquids. In other words, the fist containing area 161 and the second containing area 171 are disposed on the substrate 12 by a standard photolithography with SU-8 photo-resist. Therefore, the liquid can be protected against evaporating by the mineral oil in the heating process of the PCR procedure.

A metal electrical conductivity of the heating coil 13 can be higher than a metal electrical conductivity of the at least one conducting wire 14. A material of the heating coil 13 may be comprise silver, copper, gold, platinum, aluminum, iron, stannum, lead or a combination thereof, and a material of the at least one conducting wire 14 may also be comprise silver, copper, gold, platinum, aluminum, iron, stannum, lead or a combination thereof. The template may comprise deoxyribonucleic acid (DNA) or ribonucleic acid (RNA). If the template is DNA, the traditional PCR can be performed; otherwise, if the template is RNA, such as mRNA, the reverse transcription PCR can be performed. Additionally, a shape of the heating coil may comprise a circle, an angle, or an irregular shape. A material of the substrate 13 may comprise silica, glass, nylon, polymer, or ceramic, and a material of the cooling plate 11 may comprise Si/Quartz.

However, the plurality of sensors 15 are disposed around the heating coil 13 to accurately control temperatures. The temperatures can be calculated accurately by the following formula.

$$R_T = R_0[1+\alpha(T-T_0)]$$

Wherein, in the above formula, $R_T$ is a resistance value at the temperature T, $R_0$ is a temperature resistance value at the temperature $T_0$, and $\alpha$ is a temperature conductivity coefficient. The plurality of sensors 15 can detect the resistance value while heating the heating coil 13. In other words, when metals are heated, the resistance value of the metals will be changed, such that, by the above formula, the resistance value can be calculated to get a certain temperature of the liquid.

Figure 3:
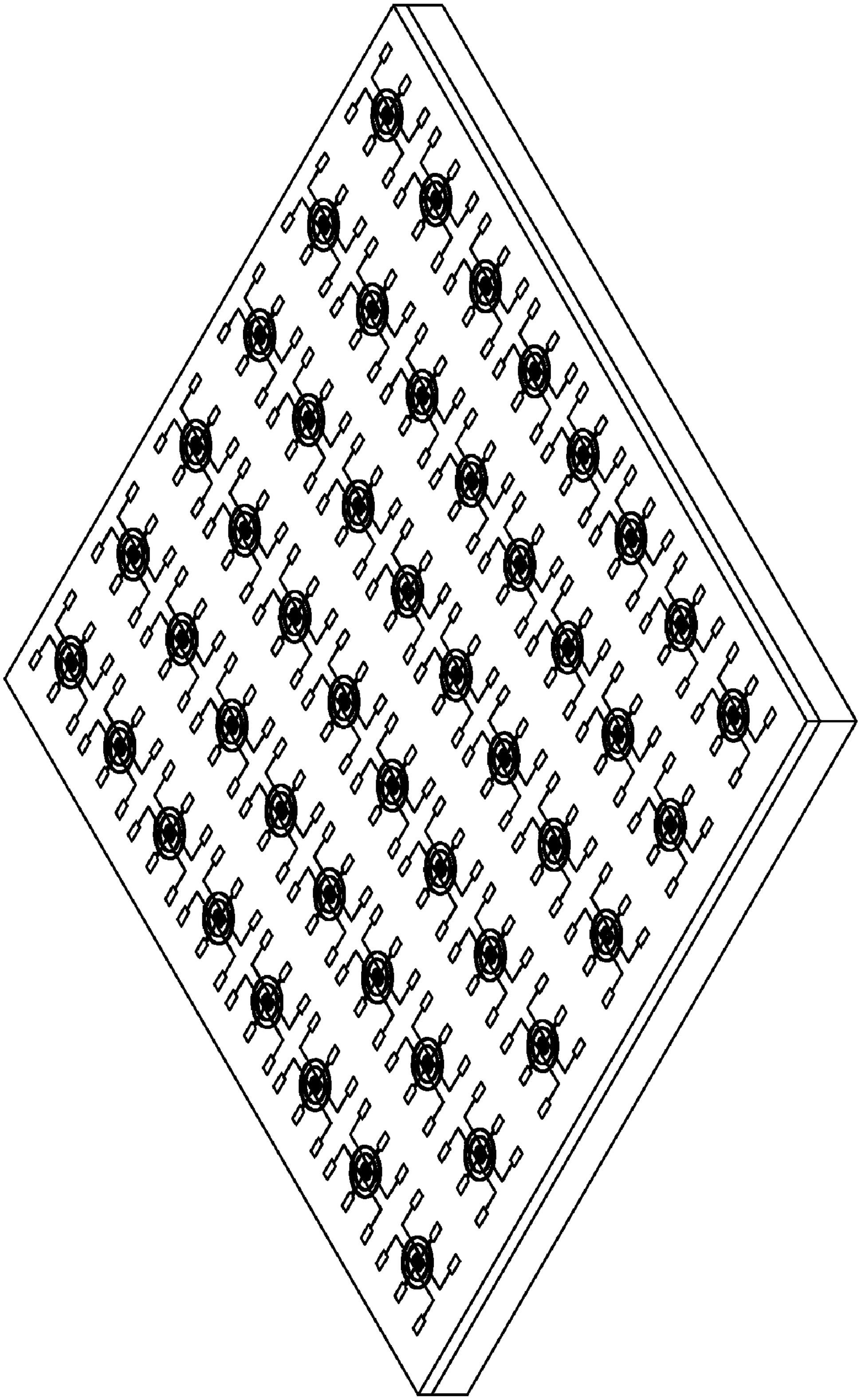
FIG. 3 is a schematic diagram illustrating a PCR droplet device array according to an embodiment of the present invention.

Please refer to FIG. 3, a schematic diagram illustrating a PCR droplet device array according to an embodiment of the present invention is shown. The plurality of PCR droplet devices as set forth are disposed in an array mode. Many kinds of samples can be experimented on the PCR droplet device array, and in the meanwhile, the annealing temperatures of kinds of primers can be detected. Thus, it can save the experimental time.

Figure 4:
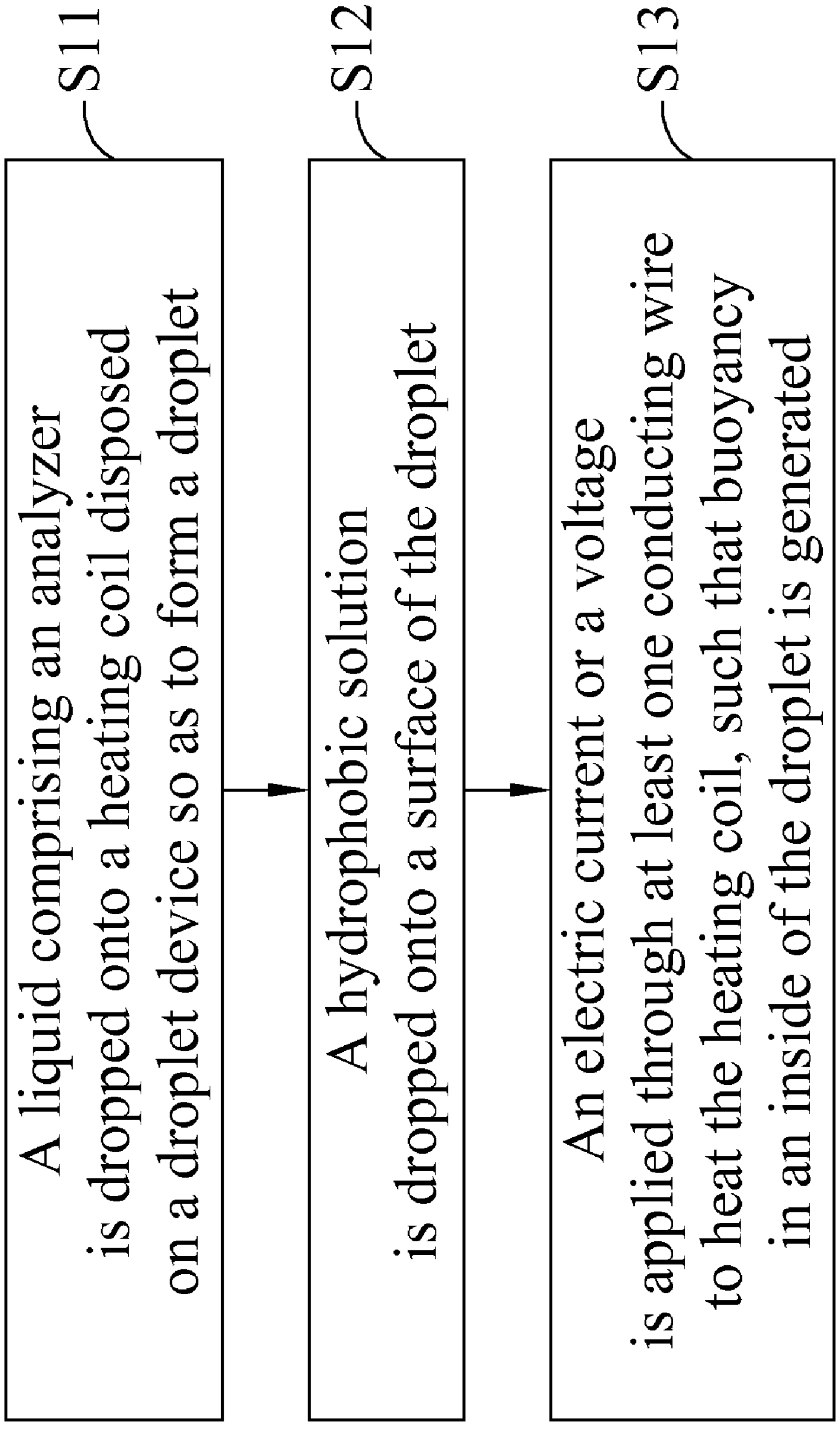
FIG. 4 is a flowchart of a PCR method according to the present invention.

Please refer to FIG. 4 that is a flowchart of a PCR method according to the present invention. As shown, the steps include as follows. In the step S11, a liquid comprising an analyzer is dropped onto a heating coil 13 to form a droplet 21. The analyzer comprises a template, a primer, a dNTP, and a polymerase, and the liquid can comprise glycerol to increase the viscosity of the liquid, such that users can adjust the retention time of the analyzer at the specific temperature. In the step S12, a hydrophobic solution is dropped onto a surface of the droplet to prevent the liquid from evaporating. In the step S13, an electric current or a voltage is applied through at least one conducting wire 14 to heat the heating coil 13. When the inside of the droplet 21 is heated, buoyancy is generated, thereby driving the analyzer to move to a top 212 of the inside of the droplet. Subsequently, the analyzer is moved to a periphery of the inside of the droplet so as to form a thermal cycle.

Figure 5:
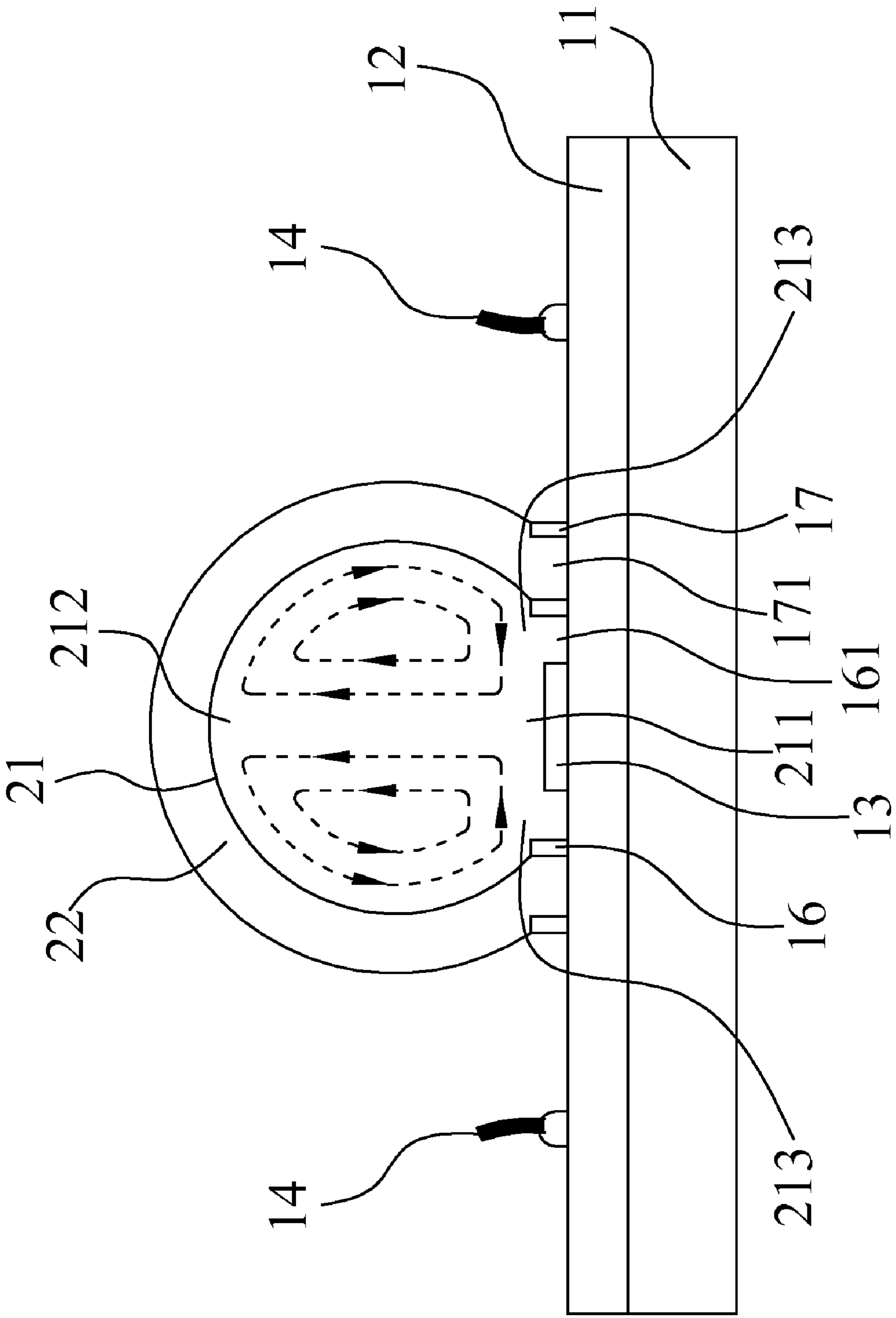
FIG. 5 is a schematic diagram of thermal cycling trails in a droplet reacted on a PCR droplet device according to the present invention.

Wherein, a temperature of a center 211*of* a bottom of the droplet 21 is in a range of 90 to 100° C. to denature the template, and the analyzer is moved to the top 212 of the inside of the droplet 21 by the buoyancy. Further, a temperature of the top 212 of the inside of the droplet 21 is in a range of 30 to 65° C. to anneal the primer on a specific position of the template. Subsequently, the analyzer is moved to a side 213 of the bottom of the droplet 21 by the circular shape of the droplet 21. A temperature of the side 213 of the bottom of the droplet 21 is in a rage of 65 to 80° C. so as to extend the specific position of the template. Finally, the analyzer is moved back to the center 211 of the bottom of the droplet 21 to form the thermal cycle, as shown in FIG. 5. Therefore, the template is amplified by recycling the thermal cycle.

Preferably, the hydrophobic solution may be mineral oil to prevent the liquid comprising the analyzer from evaporating in the PCR procedure. A metal electrical conductivity of said heating coil 13 can be higher than a metal electrical conductivity of the at least one conducting wire 14. Thus, a material of the heating coil 13 may be comprise silver, copper, gold, platinum, aluminum, iron, stannum, lead or a combination thereof, and a material of the at least one conducting wire 14 may also be comprise silver, copper, gold, platinum, aluminum, iron, stannum, lead or a combination thereof. The template may comprise DNA or RNA. If the template is DNA, the traditional PCR procedure cam be performed, otherwise, if the template is RNA, such as mRNA, the reverse transcription PCR procedure can be performed. Additionally, a shape of the heating coil may comprise a circle, an angle, or an irregular shape. Therefore, an electric current or a voltage is applied through at least one conducting wire 14 to heat the heating coil 13. The flow field inside of the droplet and temperatures thereof are changed by heating the heating coil 13 so as to generate thermal cycling trails. The amplification of the template is accomplished by recycling the thermal cycle.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A polymerase chain reaction (PCR) droplet device, comprising:

a cooling plate;

a substrate disposed on the cooling plate;

a first containing area disposed on the substrate to contain a liquid comprising an analyzer;

a second containing area disposed on the substrate, and the second containing area surrounding the first containing area to contain a hydrophobic solution, wherein the hydrophobic solution is located at a surface of the liquid;

a heating coil disposed on a center of the first containing area and the heating coil is located inside the first containing area;

at least one conducting wire disposed on the substrate and connected with the heating coil; and a plurality of sensors disposed around the heating coil to detect temperature changes of the heating coil;

wherein, the analyzer comprises a template, a primer, a deoxyribonucleotide triphosphate (dNTP) and a polymerase; the at least one conducting wire is applied with an electric current or a voltage to heat the heating coil such that buoyancy in an inside of the liquid is generated, thereby driving the analyzer to move to a top of the inside of the liquid and subsequently to move to a periphery of the inside of the liquid so as to form a thermal cycle; and the template is amplified by recycling the thermal cycle;

wherein, a metal electrical conductivity of the heating coil is higher than a metal electrical conductivity of the at least one conducting wire.

2. The PCR droplet device as claimed in claim 1, wherein the first containing area is formed by a first partition surrounding a periphery of the heating coil.

3. The PCR droplet device as claimed in claim 2, wherein a distance between the first partition and the heating coil is in a range of 0.5 to 2.5 mm.

4. The PCR droplet device as claimed in claim 3, wherein the second containing area is formed by a second partition surrounding a periphery of the first partition.

5. The PCR droplet device as claimed in claim 4, wherein a distance between the second partition and the heating coil is in a range of 1 to 3 mm.

6. The PCR droplet device as claimed in claim 1, wherein the first containing area is coated with a hydrophilic material.

7. The PCR droplet device as claimed in claim 6, wherein a functional group of the hydrophilic material comprises a hydrogen group, a carbonyl group, a carboxyl group, hydroxyl group, a sulfonic acid group, or an amino group.

8. The PCR droplet device as claimed in claim 7, wherein the second containing area is coated with a hydrophobic material.

9. The PCR droplet device as claimed in claim 8, wherein the hydrophobic material comprises epoxide, cyclic acetal, or styrene.

10. The PCR droplet device as claimed in claim 1, wherein the hydrophobic solution comprises mineral oil.

11. The PCR droplet device as claimed in claim 1, wherein a material of the substrate comprises silica, glass, nylon, polymer, or ceramic.

12. The PCR droplet device as claimed in claim 1, wherein a material of the heating coil comprises silver, copper, gold, platinum, aluminum, iron, stannum, lead or a combination thereof.

13. The PCR droplet device as claimed in claim 12, wherein a material of the at least one conducting wire comprises silver, copper, gold, platinum, aluminum, iron, stannum, lead or a combination thereof.

14. The PCR droplet device as claimed in claim 1, wherein the template comprises deoxyribonucleic acid (DNA) or ribonucleic acid (RNA).

15. The PCR droplet device as claimed in claim 1, wherein a shape of the heating coil comprises a circle, an angle, or an irregular shape.

16. The PCR droplet device as claimed in claim 1, wherein the liquid further comprises glycerol.

17. A polymerase chain reaction (PCR) droplet device array comprising a plurality of the PCR droplet device as claim 1, and the plurality of the PCR droplet devices disposed in an array mode.

* * * * *